United States Patent [19]

Kordes et al.

[11] Patent Number: Plant 5,679

[45] Date of Patent: Mar. 4, 1986

[54] ROSE PLANT KORENLO

[75] Inventors: Reimer Kordes; Werner Kordes; Hermann Kordes, all of Klein Offenseth Sharrieshoop, Fed. Rep. of Germany

[73] Assignee: Jackson & Perkins Company, Medford, Oreg.

[21] Appl. No.: 651,680

[22] Filed: Sep. 17, 1984

[51] Int. Cl.[4] ..... A01H 5/00

[52] U.S. Cl. ..... Plt./26

[58] Field of Search ..... Plt./26

*Primary Examiner*—Robert E. Bagwill

*Attorney, Agent, or Firm*—Manford R. Haxton

[57] ABSTRACT

A floribunda rose variety having large quantities of cut blooms of mottled pink and white color, heavy petals, little fragrance on long rigid stems.

1 Drawing Figure

This present invention relates to a new and distinct variety of rose plant of the floribunda class which was originated by crossing the variety Angelique, U.S. Plant Pat. No. 5,012, with the variety (Berolina)(Banzai).

The primary objective of this breeding was to produce a new rose variety of the floribunda class, suitable for production of cut flowers in a greenhouse, with exceptional keeping quality, novel coloring and efficient production. This objective was substantially achieved along with other desirable improvements as evidenced by the following unique combination of characteristics which are outstanding in the new variety and which distinguish it from its parents as well as from all other varieties of which I am aware:

1. Its mottled pink and white buds;
2. Unusually stiff or crisp pwetals;
3. Long and stiff stems;
4. Clean, mildew resistant foliage;
5. Very little fragrance.

Asexual reproduction of this new variety by budding, as performed at Wasco, Calif., shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color in terminology in accordance with The Royal Horticultural Society Colour Chart except where ordinary dictionary significance of color is indicated:

Parentage:

*Seed parent.*—Angelique, U.S. Plant Pat. No. 5,012.

*Pollen parent.*—(Berolina)(Banzai).

Classification:

*Botanical.*—Rosa hybrid.

*Commercial.*—Floribunda.

FLOWER

Observations made from specimens grown in a greenhouse at Irvine, Calif. in July.

Blooming habit: Continuous.

Bud:

*Size.*—1¼" when petals start to unfurl.

*Form.*—Long, blunt top.

*Color.*—When sepals first divide, Mottled Red 55A over white with larger white streaks near midribs; when half blown, upper side of petals Mottled Red 55B over white; lower side of petals Mottled Red 55B over white, with less Mottled Red and more white than on upper side.

*Sepals.*—Color: Green 138A. Three appendaged sepals lightly appendaged. Two appendaged sepals hairy edged.

*Receptacle.*—Color: Green 138A. Shape: Funnel. Size: Small. Surface: Smooth.

*Peduncle.*—Length: Medium. Surface: Nearly smooth, with few prickles. Color: Medium green. Strength: Stiff, erect.

Open bloom:

*Size.*—Medium. Average open size 3".

*Borne.*—Mostly singly.

*Stems.*—Long, strong.

*Form.*—When first open, high center, Permanence: All petals curl.

*Petalage.*—Number of petals under normal conditions: 25-30.

*Color.*—Center of flower: Upper side of petals, near white; reverse side of petals, near white. Base of petals, white. Outer half of petals: Red 55B, upper side; Mottled Red 55B on lower side; Major color, Red 55B.

*Variegations.*—Much mottling.

*Discoloration.*—General tonality at end of third day: Red 55C to 55D on both sides of petal.

*Fragrance.*—None.

Petals:

*Texture.*—Thick.

*Shape.*—Round.

*Form.*—Edges slightly quilled.

*Arrangement.*—Imbricated. Petaloids in center, few.

*Persistence.*—Drop off cleanly.

*Lastingness.*—On the plant, very long. As cut flower, very long.

Reproductive parts:

*Anthers.*—Large, many. Color: Yellow. Arrangement: Regular around styles.

*Filaments.*—Color: Light yellow.

*Pollen.*—Lemon yellow.

*Styles.*—Color: Mostly reddish — base near white.

*Stigmas.*—Color: White.

PLANT

Form: Bush.
Growth: Very vigorous, upright.
Foliage: Number of leaflets on normal mid-stem leaves: 5 or 7.
*Size.*—Large.
*Quantity.*—Normal.
*Color.*—New foliage: Green overlaid with Greyed Purple 183A. Old foliage: Normal green.
Leaflets:
*Shape.*—Elliptic.
*Texture.*—Leathery.
*Edge.*—Serrated.
*Serration.*—Single.
*Petiole.*—Rachis: Color: Green. Upperside: Two rows of glands. Underside: With prickles.
*Stipules.*—Medium, bearded.
*Disease resistance.*—Normally resistant to mildew, under normal growing conditions at Irvine, Calif.

Wood:
*New wood.*—Color: Light green. Bark: Smooth.
*Old wood.*—Color: Green. Bark: Smooth.
Prickles:
*Quantity.*—On main canes from base: Many to ordinary. On laterals from main canes: Ordinary to few. Bases of canes more heavily prickled than upper cuttable stems.
*Form.*—Long, straight.
*Color when young.*—Brown.
Small prickles:
*Quantity.*—On main stalks, none. On laterals, none.

I claim:

1. A new and distinct variety of rose plant of the floribunda class, substantially as herein shown and described, characterized particularly as to novelty by the unique combination of its ability to produce large quantities of cut blooms of mottled pink and white color, heavy petals, little fragrance on long rigid stems.

* * * * *

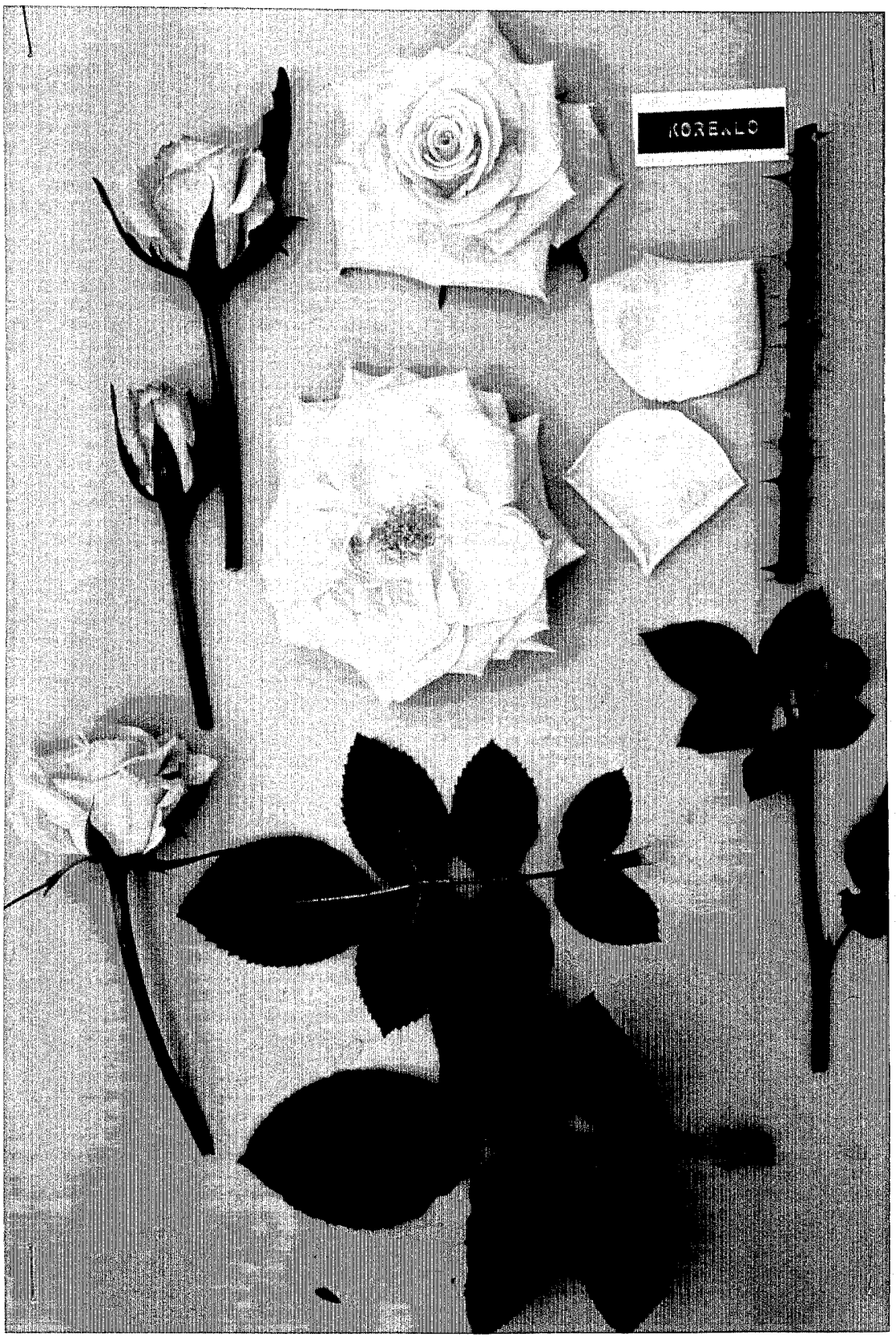
KORELLO